US010758197B2

(12) United States Patent
Richard et al.

(10) Patent No.: US 10,758,197 B2
(45) Date of Patent: Sep. 1, 2020

(54) RADIATION TRACKING FOR PORTABLE FLUOROSCOPY X-RAY IMAGING SYSTEM

(71) Applicant: CARESTREAM HEALTH, INC., Rochester, NY (US)

(72) Inventors: Samuel Richard, Rochester, NY (US); Xiaohui Wang, Pittsford, NY (US); Michael C. Lalena, Webster, NY (US)

(73) Assignee: Carestream Health, Inc., Rochester, NY (US)

(*) Notice: Subject to any disclaimer, the term of this patent is extended or adjusted under 35 U.S.C. 154(b) by 0 days.

(21) Appl. No.: 16/221,662

(22) Filed: Dec. 17, 2018

(65) Prior Publication Data

US 2019/0380668 A1    Dec. 19, 2019

Related U.S. Application Data

(60) Provisional application No. 62/685,473, filed on Jun. 15, 2018.

(51) Int. Cl.
*A61B 6/02* (2006.01)
*A61B 6/00* (2006.01)
*A61B 6/08* (2006.01)

(52) U.S. Cl.
CPC .......... *A61B 6/485* (2013.01); *A61B 6/08* (2013.01); *A61B 6/4405* (2013.01); *A61B 6/487* (2013.01); *A61B 6/542* (2013.01); *A61B 6/545* (2013.01); *A61B 6/547* (2013.01); *A61B 6/465* (2013.01); *A61B 6/587* (2013.01); *A61B 6/588* (2013.01)

(58) Field of Classification Search
CPC ....... A61B 6/458; A61B 6/4405; A61B 6/542; A61B 6/08; A61B 6/547; A61B 6/487; A61B 6/465; A61B 6/588; A61B 6/587; A61B 6/10; A61B 6/4452; A61B 6/488; A61B 6/545
See application file for complete search history.

(56) References Cited

U.S. PATENT DOCUMENTS

| 8,821,017 | B2 | 9/2014 | Lalena et al. | |
|---|---|---|---|---|
| 8,873,712 | B2 | 10/2014 | Wang et al. | |
| 9,693,746 | B2 | 7/2017 | Ancar | |
| 9,788,810 | B2 | 10/2017 | Ancar | |
| 9,918,684 | B2 | 3/2018 | Ancar | |
| 2011/0158385 | A1 | 6/2011 | Nakatsugawa et al. | |
| 2013/0182823 | A1* | 7/2013 | Kuwabara | A61B 6/542 378/62 |
| 2015/0374314 | A1* | 12/2015 | Maack | A61B 6/06 378/62 |
| 2017/0265826 | A1 | 9/2017 | Ancar | |
| 2018/0092613 | A1 | 4/2018 | Ancar | |
| 2018/0153488 | A1 | 6/2018 | Ancar | |

OTHER PUBLICATIONS

International Search Report dated Aug. 5, 2019 for International Application No. PCT/US2019/035917, 2 Pages.
Commonly assigned PCT Application No. PCT/US18/24274, entitled Bedside Dynamic Imaging, filed on Mar. 26, 2018, by Dennis J. O'Dea et al.

* cited by examiner

*Primary Examiner* — Kiho Kim

(57) ABSTRACT

A method for fluoroscopy energizes a radiation source to form a scout image on a detector and processes the scout image to determine and report a radiation field position with respect to a predetermined zone of the detector. The radiation source is energized for fluoroscopic imaging of a subject when the reported radiation field position is fully within the predetermined zone.

24 Claims, 14 Drawing Sheets

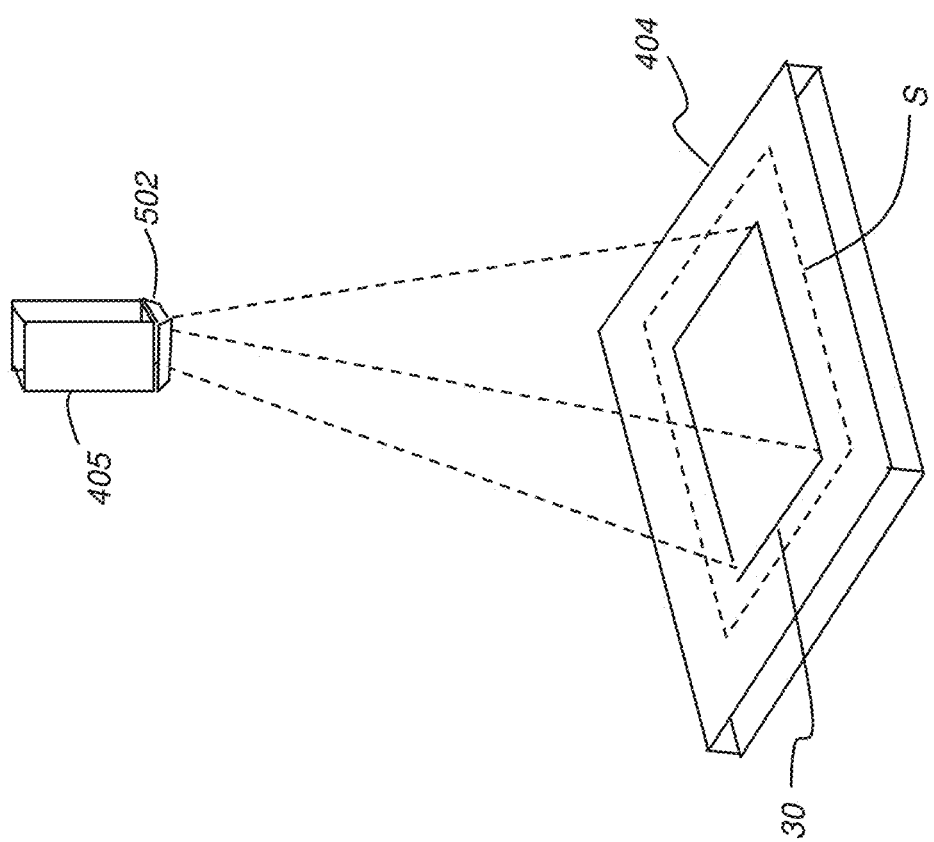

RADIATION TRACKING FOR PORTABLE FLUOROSCOPY X-RAY IMAGING SYSTEM

CROSS REFERENCE TO RELATED APPLICATIONS

This application claims the benefit of U.S. Provisional application U.S. Ser. No. 62/685,473, provisionally filed on Jun. 15, 2018, entitled "RADIATION TRACKING FOR PORTABLE FLUOROSCOPY X-RAY IMAGING SYSTEM", in the names of Richard et al., incorporated herein in its entirety.

TECHNICAL FIELD

The disclosure relates generally to the field of digital medical imaging and in particular to digital medical imaging for fluoroscopy. More specifically, the disclosure relates to a radiation source tracking method for a portable fluoroscopy x-ray imaging system.

BACKGROUND

Fluoroscopic imaging is valued as a useful tool for practitioner guidance during surgery or other interventional or diagnostic procedure. Using fluoroscopic apparatus, the practitioner can obtain real-time video feedback on aspects of a surgical procedure, on positioning of tubing or other hardware, flow of a contrast agent, or activity of a particular organ. In conventional fluoroscopic imaging systems, the radiation source and detector are mechanically coupled, so that their position, relative to each other, has a rigid, fixed geometry. Alignment of the x-ray source to detector is not adjustable to the operator, but is fixed by the imaging system mechanics.

The advent of portable digital radiography (DR) detectors advances radiographic imaging and makes it possible to improve patient access to imaging services, such as in situations where it can be risky or awkward to move the patient for a procedure. An area where this can be of particular utility is in the intensive care unit (ICU), where multiple support systems may need to be used for a particular patient.

One difficulty with the use of portable DR detectors relates to data on relative source-to-detector positioning, which is no longer inherently provided by the imaging system. Aspects of positioning that are of particular importance for fluoroscopy include positioning the source so that it is perpendicular with the detector and field limitation, controlling the radiation field size and direction so that the primary radiation field lies fully on the detector.

Various source-detector alignment approaches have been proposed for systems having the DR detector mechanically decoupled from the source. These approaches have included the use of various instruments to detect skew, orientation, source-image distance, and other aspects of positioning for these components. Other approaches have included the use of an initial exposure that directs a pattern of alignment beams toward the detector for sensing and calculation of skew error. While there is some merit in such approaches, however, they are largely directed to portable radiography itself, rather than to specific requirements of fluoroscopy. Characterized by lower levels of radiation and real-time display of image content at lower resolution, fluoroscopy is a guidance tool that helps the practitioner to visualize the progress of a procedure rather than to diagnose the condition of internal bone or tissue.

There are a number of considerations and requirements of conventional radiographic practice that are poorly suited for the fluoroscopy environment. This can be appreciated, for example, in considering differences between serial radiography, in which a series of exposures is acquired in a timed sequence using standard radiographic strictures, and fluoroscopy, in which a series of exposures is rapidly acquired under very different working conditions and generally at lower dosage and, consequently, lower resolution. In serial radiography, the radiographer and any attending staff move away from the imaged subject until the series of exposures completes and the images are generated and displayed. In fluoroscopy, on the other hand, the sequence of exposures is acquired and displayed with the practitioner and staff positioned closely about the patient and, consequently, very near to the radiation field.

Distinctions between radiography and fluoroscopy environments and practices have been recognized by regulatory agencies, along with an awareness of the advantages and risks of portable detector use. As one result, there are different requirements for beam accuracy in light of these differences.

FIG. 1 summarizes some of the separate regulatory requirements that have been adopted for radiographic and fluoroscopic devices. Under the radiography regulations certain exemptions are given for devices using portable detectors. The exemptions relate to risk/benefits concerns for the patient, obtained when source and detector are uncoupled, which enables imaging at a beside but limits the ability to meet certain regulations. Specifically, exemptions deal with field limitation and radiation path perpendicularity. As such, there are challenges, when using fluoroscopy with a portable detector, in meeting equivalent requirements related to conventional fluoroscopic regulations.

It may not always be possible to fix the relative positions of source and detector relative to the patient for the full fluoroscopy sequence. For example, in ICU and other environments in which fluoroscopy is used, there can be unwanted movement by the patient and the need for readjustment of source position during the imaging session. Repositioning may alternately be needed in fluoroscopy for various reasons, such as when the source or its supporting structure is accidentally jostled and shifted in position during a procedure.

Thus, it can be recognized that there is a need for solutions that meet regulatory guidelines for beam coverage and perpendicularity with portable DR detectors used in fluoroscopy applications. Of particular concern is the need to provide fluoroscopy using portable DR detectors while limiting exposure to the treatment region and away from the attending medical team and from other regions of patient anatomy.

SUMMARY

An object of the present disclosure is to address the need for improved radiation tracking for fluoroscopy x-ray imaging systems using portable DR detectors.

These objects are given only by way of illustrative example, and such objects may be exemplary of one or more embodiments of the disclosure. Other desirable objectives and advantages inherently achieved by the may occur or become apparent to those skilled in the art. The disclosure is defined by the appended claims.

According to an aspect of the present disclosure, there is provided a method for fluoroscopy comprising: energizing a radiation source to form a scout image on a detector;

processing the scout image to determine and report a radiation field position with respect to a predetermined zone of the detector; and energizing the radiation source for fluoroscopic imaging of a subject when the reported radiation field position is fully within the predetermined zone.

BRIEF DESCRIPTION OF THE DRAWINGS

The foregoing and other objects, features, and advantages of the invention will be apparent from the following more particular description of exemplary embodiments of the invention, as illustrated in the accompanying drawings. The elements of the drawings are not necessarily to scale relative to each other.

FIG. 10A is a perspective view showing an outline of a radiation field in a Safe zone defined on the detector.

DETAILED DESCRIPTION OF THE EMBODIMENTS

Figure 1:
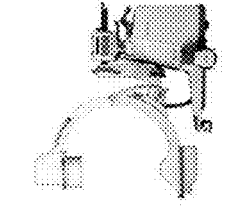
FIG. 1 is a chart that gives a summary view of the regulatory landscape for radiography and fluoroscopy systems using fixed and portable detectors.

The following is a detailed description of the preferred embodiments, reference being made to the drawings in which the same reference numerals identify the same elements of structure in each of the several figures.

In this document, the terms "a" or "an" are used, as is common in patent documents, to include one or more than one, independent of any other instances or usages of "at least one" or "one or more". In this document, the term "or" is used to refer to a nonexclusive or, such that "A or B" includes "A but not B", "B but not A", and "A and B", unless otherwise indicated. In this document, the terms "including" and "in which" are used as the plain-English equivalents of the respective terms "comprising" and "wherein". Also, in the following claims, the terms "including" and "comprising" are open-ended, that is, a system, device, article, or process that includes elements in addition to those listed after such a term in a claim are still deemed to fall within the scope of that claim.

In the following claims, the terms "first", "second", and "third", and the like, are used merely as labels, and are not intended to impose numerical or ordinal requirements on their objects.

In the context of the present disclosure, the terms "viewer", "operator", "viewing practitioner", "observer", and "user" are considered to be equivalent and refer to the viewing practitioner or other person who views and manipulates an x-ray image on a display monitor or other viewing apparatus.

As used herein, the term "energizable" relates to a device or set of components configured to perform an indicated function upon receiving power and, optionally, upon receiving an enabling signal.

The term "actuable" has its conventional meaning, relating to a device or component that is capable of effecting an action in response to a stimulus, such as in response to an electrical signal, for example.

The term "modality" is a term of art that refers to modes or types of imaging. Modalities for an imaging system may be conventional x-ray radiography, fluoroscopy or pulsed radiography, tomosynthesis, tomography, ultrasound, MMR, or other types of imaging. The term "subject" refers to the patient who is being imaged and, in optical terms, can be considered equivalent to the "object" of the corresponding imaging system.

The terms "image" and "image data" can be used interchangeably in the context of the present disclosure. An image that is captured by an imaging apparatus is processed, displayed, transmitted, and stored as image data.

Applicants' disclosure is directed to satisfying performance objectives of fluoroscopy regulations while maintaining advantages of the decoupled detector. Applicants' disclosure focuses on field limitation, which ensures that the primary radiation is directed fully within the detector boundary during fluoroscopic captures.

Proper field limitation ensures that all of the primary radiation of the radiation field is contained within the image receptor. This is important so as to minimize dose to the patient and reduce exposure risk to the staff.

Fluoroscopy differs from conventional radiography in a number of ways. In fluoroscopic imaging, for example, an operator control, typically a foot pedal as described subsequently, is used as a type of switch for energizing the radiation source to generate exposures. According to an embodiment of the present disclosure, this operator control is enabled when the detected radiation field is in appropriate position relative to the detector. This can mean that the energization current is available for energizing x-ray emission when these field conditions are determined. Operation of the foot pedal or other control then causes the circuit connection to complete, so that the radiation source is energized and emits radiation. If the control is disabled, the operator cannot cause x-ray emission to occur without using an override control or command.

With conventional workflow, fluoroscopy systems typically do not include a collimator light field. Conventional fluoroscopy systems direct radiation through the patient to an electronic detector that provides video output on a display monitor. The extent of the x-ray source field or field boundaries are often not visible to the operator. Therefore, for such systems, initial setup is performed by visually aligning the fluoroscopy assembly to the patient. At this point, acquisition of a single fluoroscopy image frame, or of a few exposures, confirms initial positioning. Adjustments are made and the exposure level is set via an automatic brightness control. Field limitation is automatically achieved via the structural linkage, with fixed positioning maintained between radiation source and detector.

Applicants' disclosure provides/describes an alternate workflow to provide suitable field limitation with a portable DR detector.

Applicants note that fluoroscopy requires that the x-ray source/tube and detector be aligned such that all of the x-ray radiation field is captured by the digital detector. This alignment is inherent in conventional fluoroscopy systems when source and detector are mechanically coupled. However, systems using portable DR detectors that are not mechanically coupled to the source are not able to readily determine or provide source/detector alignment and consequent control of radiation field position prior to imaging. This disclosure provides a method to track, warn, and/or terminate the x-ray radiation if the radiation field impinges upon or exceeds predetermined/preset boundaries of the portable DR detector. More particularly, x-ray emission from the tube/source is terminated automatically if the radiation field impinges and/or falls outside of the digital detector. Applicants' method thus does not require the use of a mechanical linkage between the tube/source and digital detector for sensing incorrect positioning of the radiation field.

According to an embodiment of the present disclosure, visible illumination, coupled to the x-ray source and emitted through the collimator, can be used to help guide source positioning. While in the fluoroscopy mode, the collimator illumination is automatically turned on to provide assistance for positioning the tube over the patient and the detector.

The collimator illumination remains on throughout the fluoroscopy exam. In addition, the appearance of the collimator illumination can be changed to indicate the status of radiation field positioning. Thus, for example, the collimator illumination can be white light when the radiation field is detected in a suitable position for fluoroscopy, such as within the Safe zone, as described subsequently. Detection of the radiation field within other zones of the detector, such as the Warning and Termination zones described subsequently, can cause a change in the illumination color. Appearance change can also relate to blinking, intensity variation, patterning, or other feature of the illumination or portions of the illumination field.

A scout image, which is a low-dose radiograph optimized for the region being imaged, is acquired both (i) to confirm position and, additionally, (ii) to assess the field limits. The scout image is acquired with one set of technique settings, such as can be used for radiographic imaging, for example. Subsequent fluoroscopy imaging can then use a different set of technique settings. The scout and fluoroscopy images can have the same field dimensions.

Software automatically analyzes the scout image to ensure that the entire radiation field is within the boundary of the detector. The system does not enable fluoroscopic acquisition until this condition is met.

Because the majority of system technicians/operators are currently trained to use a light field for portable radiography alignment and because the detector is larger than the typical ROI (Region of Interest) for a fluoroscopic procedure, the likelihood of the radiation field being outside the detector during scout image acquisition is expected to be low.

According to an embodiment of the present disclosure, the relative position of the radiation field is tracked by defining and monitoring a series of zones within the digital radiography detector. Zones are defined and prioritized based on relative proximity to outer edges of the detector. Detection of radiation in the outermost zones, nearest the edges, indicates the need to adjust the position of the x-ray source or to de-energize the x-ray source altogether, terminating fluoroscopy imaging until positioning of the radiation field is corrected. Thus, as to radiation tracking during fluoroscopy, tracking of the radiation during fluoroscopic acquisition is used to provide warning and termination (an optional feature/step/process) of the x-ray under certain conditions. The sequence of FIGS. 2, 3, 4, and 5 describes examples of different possible conditions for x-ray field positioning.

Figure 2:
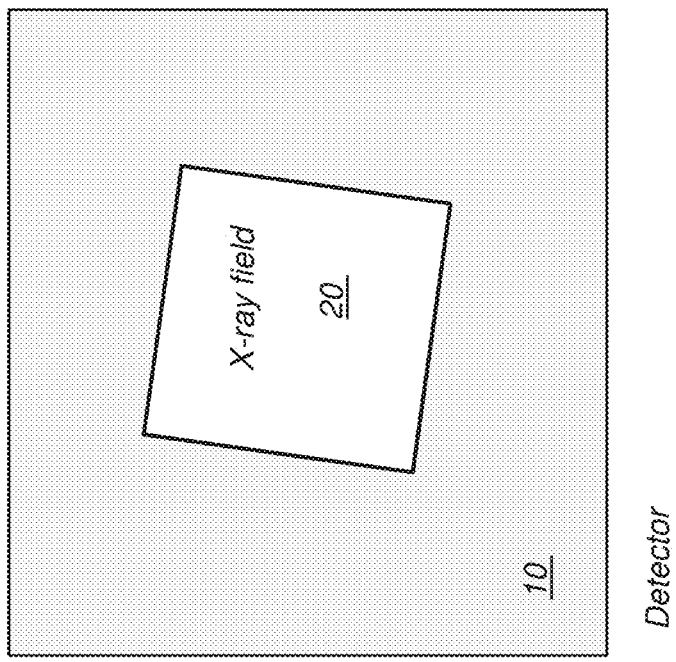
FIG. 2 is a schematic diagram that shows an x-ray imaging field incident on the active imaging area of a digital radiography detector.

For example, referring to FIG. 2, there is illustrated an x-ray imaging field 20 incident on the active imaging area of a digital radiography detector 10. Although radiation field 20 may be skewed with respect to the edge borders or outline of the active DR detector 10 imaging field, the full field 20 lies well within the active DR detector 10 imaging field.

Figure 3:
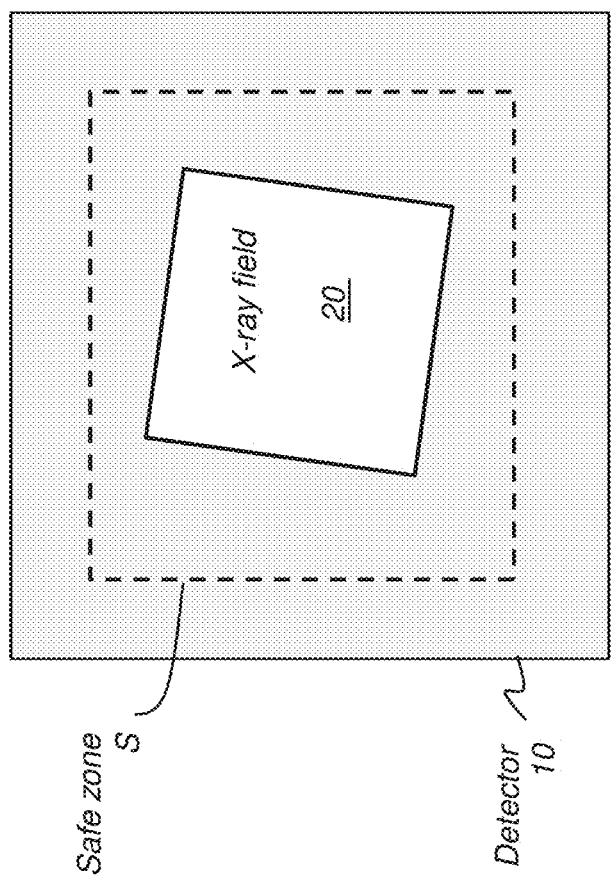
FIG. 3 is a schematic diagram that shows an x-ray imaging field incident on the active imaging area and within a safe zone of a digital radiography detector.

Referring to the example of FIG. 3, the preferred position of x-ray field 20 is within a safe zone S of detector 10, shown in dashed outline. The technician or other operator of a fluoroscopy system typically aims x-ray field 20 so that the primary radiation is incident on detector 10, with none of x-ray field precariously close to, or lying beyond, any edge of detector 10. The safe zone S region that is defined for fluoroscopy is disposed well within the available imaging field of the detector as shown.

Figure 4:
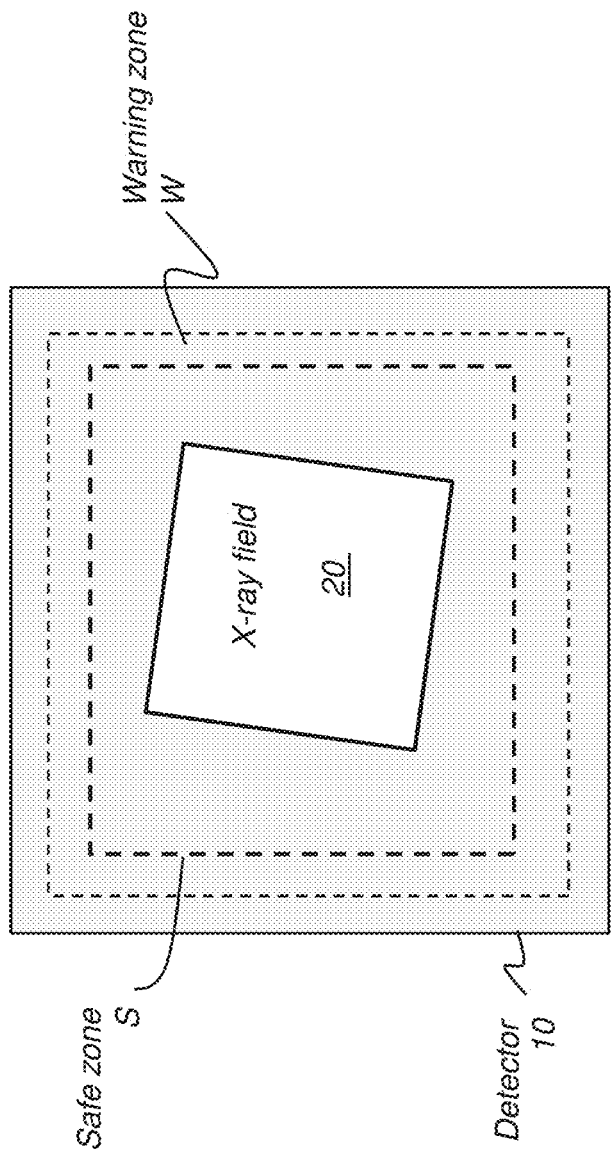
FIG. 4 is a schematic diagram that shows an x-ray imaging field incident on the active imaging area and within a warning zone of a digital radiography detector.

Referring to the schematic diagram of FIG. 4, a second region is defined, Warning zone W, extending from the periphery of the safe zone S and still within the active imaging area of the detector 10. In a preferred arrangement, the Warning zone W is a few centimeters wide, which can be suitable for conventional fluoroscopy applications; dimensions for defining zone W boundaries can vary widely, as can be readily appreciated by those skilled in the radiographic arts. Preferably, the Warning zone W surrounds all sides/edges/boundaries of the Safe zone S. In an alternate embodiment, it may be sufficient to define the Warning zone W along at least one side/edge/boundary of the Safe zone S.

In a preferred arrangement, if any portion of the primary/designated x-ray radiation field 20 is incident within Warning zone W, a warning signal is generated and a warning message or other warning indication results and is reported, displayed to the operator. Such a warning indication could be audible or visible, for example. A visible warning could include a message, text, symbol, icon, marker or the like displayed on a monitor/display or projected to appear on the patient. Similarly, the warning could be a message, text, symbol, icon, marker or the like sent to the user's mobile device/tablet.

According to an alternate embodiment of the present disclosure, a warning indication can also be provided by a collimator light that provides illumination that is visible to one or more members of the fluoroscopy team. The color of the collimator light can be changed to indicate a warning condition; alternately, flashing or other light behavior can be used for warning indication.

Figure 5:
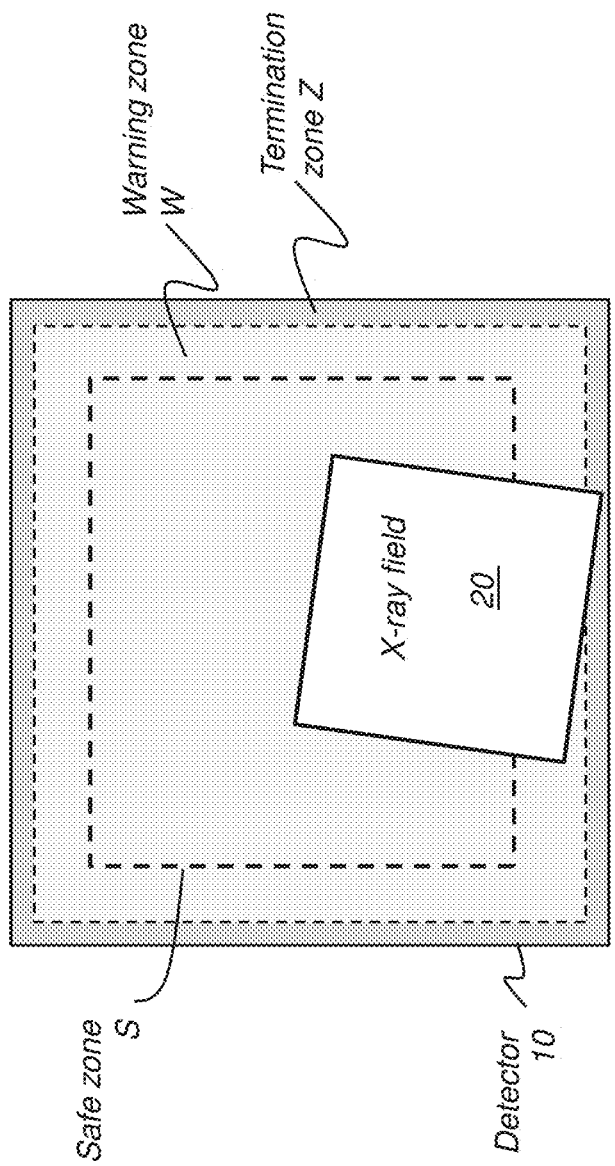
FIG. 5 is a schematic diagram that shows an x-ray imaging field incident on the active imaging area and extending into a termination zone of a digital radiography detector.

Referring to FIG. 5, a third/another region, extending from the outer boundary of the Warning zone W to the inner edges of the detector 10 imaging area, serves as a termination zone Z. If any portion of the radiation field primary/designated beam extends into Termination zone Z, there is the potential for some portion of the exposure energy to be misdirected past an edge of DR detector 10. To prevent this condition, control logic for the fluoroscopy apparatus can continually sense for any portion of the emitted radiation field in zone Z and generate an appropriate signal for reporting positioning status.

In the event of detection of x-ray radiation within Termination zone Z, x-ray energy is turned off. Following this action, after correcting the aim or alignment of the source, the user/operator could immediately resume the study by initiating a scout image. The Termination zone Z is disposed within the detector field.

Optionally, a warning can be displayed to the operator when the radiation field extends outside of the Safe zone S to either or both Warning zone W and Termination zone Z. Such a warning could be audible or visible. A visible warning could include as a message, text, symbol, icon, marker or the like displayed on a monitor/display. Similarly, it could be a message, text, symbol, icon, marker or the like sent to the user's mobile device/tablet. The warning may include instructions to the user/operator to immediately resume the study with a scout image. Alternately, an indication could be projected onto the surface of the patient, using the collimator light or a related projector.

In a preferred arrangement, the Termination zone Z can be a few centimeters wide. Preferably, the Termination zone Z surrounds all sides/edges/boundaries of the Warning zone W. In an alternate embodiment, it may be sufficient to define the termination zone Z along at least one side or edge of the warning zone W.

In addition, the collimator light that shows the radiation field boundaries can remain on continuously, or can be flashing, during and between acquisitions in fluoroscopic mode, providing instant visual feedback on positioning to the practitioner and staff. Additional feedback can be provided by changing color of the collimator illumination, such as to indicate whether or not the radiation field is detected solely within the Safe zone S or impinges upon Warning zone W or Termination zone Z.

This disclosure describes a system and method of radiation tracking for a portable fluoroscopy x-ray imaging system, wherein the system comprises an x-ray source, a collimator, and a freely positionable DR detector that is uncoupled from the x-ray source. The method includes: positioning the x-ray source and the DR detector about a patient; adjusting an aperture of the collimator to a predetermined size known to generate an x-ray radiation field to substantially fit within the borders of the DR detector; determining a Safe zone region surrounding the x-ray radiation field and within the borders of the detector; determining a Warning zone region surrounding the Safe zone and fully within the borders of the detector; determining a Termination zone region surrounding the Warning zone; and operating the imaging system in a fluoroscopy mode by: (i) activating the x-ray source; (ii) using the activated x-ray source, iteratively acquiring a digital image on the DR detector; (iii) determining if the x-ray radiation field of the x-ray source used to acquire the digital image impinges the Safe zone, Warning zone, or Termination zone; (iv) providing a warning if the x-ray radiation field impinges the Safe zone or Warning zone, and (v) deactivating the x-ray source if the x-ray radiation impinges the Termination zone.

Reference is made to PCT/US18/24274, filed on Mar. 26, 2018, entitled BEDSIDE DYNAMIC IMAGING, in the names of O'Dea et al, incorporated herein in its entirety by reference.

When an x-ray image is obtained, there is generally an optimal distance and angle between the radiation source and the two-dimensional digital radiography (DR) detector that records the image data. In most cases, it is preferred that the x-ray source provide radiation in a direction that is generally perpendicular to the surface of the DR detector. For this reason, large-scale radiography systems mount the radiation head and the DR detector holder at a specific angle relative to each other. Orienting the radiation head and the DR detector typically requires a C-arm of substantial size, extending outward well beyond the full distance between these two components. With such large-scale systems, source-to-image distance (SID) is tightly controlled and unwanted tilt or skew of the DR detector is thus prevented by the hardware of the imaging system itself. Further, because the spatial positioning and geometry of conventional large-scale systems is well-controlled, proper alignment of the x-ray source and DR detector is inherent and straightforward.

Mobile x-ray apparatus are of particular value in intensive care unit (ICU) and other environments where timely acquisition of a radiographic image is important. Because it can be manually wheeled around the ICU or other area and brought directly to the patient's bedside, a mobile x-ray system allows an attending physician or clinician to have up-to-date information on the condition of a patient and helps to reduce the risks entailed in moving patients to stationary equipment in the radiological facility. With the advent of mobile radiation imaging systems, such as those used in Intensive Care Unit (ICU) environments, a fixed angular relationship between the radiation source and two-dimensional DR detector, and accompanying grid, if any, is no longer maintained by the mounting hardware of the system itself. Instead, an operator is required to aim the radiation source toward the DR detector imaging surface, providing as perpendicular an orientation as possible, typically using a visual assessment. The DR detector itself, however, may not be visible to the technician once it is positioned underneath or behind the patient. This complicates the alignment task for mobile systems, requiring some method and apparatus for measuring SID (source-to-image distance) and tilt angle, and making it more difficult to use a grid effectively for reducing the effects of radiation scatter.

Current portable radiation imaging systems allow some flexibility for placement of the DR detector by the radiology technician. The patient need not be in a horizontal position for imaging, but may be at any angle, depending on the type of image that is needed and on the ability to move the patient for the x-ray examination. The technician can manually adjust the position of both the DR detector and the radiation source independently for each imaging session. Thus, it can be appreciated that a system for determining SID and angle between the radiation source and the DR detector must be able to adapt to whatever orientation is best suited for obtaining a particular radiographic image.

Referring to FIGS. 6-9, there is shown a perspective view of a mobile digital radiographic (DR) imaging system 400 that may include: a processing console 420, embodied as a wheeled mobile x-ray cart 900 having a processing system 421 that provides control logic circuitry, such as a computer or dedicated control logic unit (CPU) with electronic memory therein, a generally planar DR detector 404, an x-ray source 408 configured to generate radiographic energy, a collimator 401 to shape the x-ray beam 403 emitted by source 408, and a digital monitor 422 configured to display radiographic and fluoroscopic images captured by the DR detector 404, according to one embodiment. The processing console 420 may also include a digital monitor thereon similar in operation to the digital monitor 422. The DR detector 404 may include a two-dimensional array of addressable photosensitive cells (pixels) as described herein above. The DR detector 404 may be positioned to receive a collimated x-ray beam 403 passing through a patient 406 lying on a bed 407 during a radiographic fluoroscopy session. The mobile radiographic imaging system 400 may use an x-ray source 408 that emits collimated x-rays, e.g. an x-ray beam 403, selectively aimed at and passing through a preselected region of the subject patient 406. The DR detector 404 is positioned underneath patient 406 in a perpendicular relation, as much as possible, orthogonal to a substantially central ray 17 of the x-ray beam 403. The location of particular pixels in detector 404 may be recorded according to column and row as described herein, in order to determine a distance between selected ones of the pixels. The density of pixels in a particular DR detector is known. For example, the pixel density may include any one designed pixel density selected from a range of between about ten pixels per millimeter to about twenty pixels per millimeter in one or both rectilinear (column×row) dimensions of the planar DR detector 404.

The photosensitive cells of detector 404 are read out by digital image processing electronics described herein to be eventually displayed on the digital monitor 422 for viewing during a fluoroscopic imaging session.

The read-out electronics may communicate with a processing console 420 over a wireless transmitter to transmit fluoroscopic image data thereto.

The processing console 420 includes a processing system having electronic memory and may also be used to control the x-ray source 408, the aperture size and shape of the electronic collimator 401, and a projection angle of the x-ray beam 403 relative to the tube head 405 by manipulating the electronic collimator aperture, the tube head 405 electric current magnitude, and thus the fluence of x-rays in x-ray beam 403, and thus the energy level of the x-ray beam 403. The processing console 420 may transmit images and other data to the connected digital monitor 422 for display thereon.

The processing system of processing console 420 may also be used to selectively identify pixels in the array by a row×column index for having absorbed a particular amount of radiographic energy, such as a high intensity and energy level, and to record the row and column indices of those pixels for source-to-image distance and tilt calculations, as described herein.

A portion or all of the processing console 420 functions may reside in the detector 404 in the on-board processing system as described herein.

DR detector 404 may include a three-dimensional, or three-axis, inclinometer, which may be referred to herein as an accelerometer, inertial sensor, or tilt sensor. In one embodiment, the DR detector 404 may be configured to transmit its three-dimensional tilt coordinates to the processing console 420. In one embodiment, the DR detector 404, with an inclinometer 503 may be configured to receive three-dimensional tilt coordinates transmitted from the collimator 401, which may include its own separate three-dimensional inclinometer. In one embodiment, both the DR detector 404 and the collimator 401 may be configured to transmit their three-dimensional tilt coordinates to the processing console 420.

The recipient of the three-dimensional tilt coordinates, the processing console 420 or the DR detector 404, may be configured to calculate a respective planar position of the DR detector 404 and the collimator 401 to determine an angular displacement of the DR detector 404 and/or the collimator 401 relative to a parallel orientation thereof. The angular displacement so determined may be displayed on the monitor 422, which displacement may include a calculated displacement having a zero value which indicates that the collimator 401 and the detector 404 are disposed parallel to each other. The angular displacement may include a calculated displacement having a 30° value which indicates that the collimator 401 and the detector 404 are displaced from a parallel orientation by 30°.

The x-ray source 408 and collimator 401 taken together may be referred to herein as a tube head 405. The collimator 401 may include an electronic collimator 401 that is configured to communicate wirelessly with the detector 404 or with the processing console 420. The collimator 401 may communicate three-dimensional coordinates 505 as determined by its connected inclinometer. The collimator 401 may communicate data on positions of the collimator blades that shape its aperture, such as width and length dimensions of the collimator aperture, for example. As described herein, the collimator 401 may include a three-dimensional inclinometer configured to dynamically transmit measured three-dimensional tilt coordinates to the detector 404 and/or to the processing console 420. Collimator blades contained in the electronic collimator 401 control a shape and size of an aperture of the collimator and, thereby, an exposure area on the detector 404, which exposure area receives x-rays of the x-ray beam 403 generated and emitted by the x-ray source 408. The pixels in the exposure area, or radiation field, transition to a charged state upon receiving x-ray radiation. The collimator blades may be configured as a pair of parallel blades forming a rectangular aperture, which blades may be individually adjustable under programmed motor control.

Control instructions for adjusting the electronic collimator aperture 501 may be transmitted from the processing console 420, which may also receive positioning feedback data from the collimator 401 indicating precise height and width dimensions of the electronic collimator aperture 501, which precise height and width dimensions may then be numerically displayed on the digital display monitor 422.

A collimator light 502 can provide illumination that serves as a guide to the location of the radiation field, as well as indicating relative position of the radiation field.

The wheeled mobile cart containing processing console 420 may be used together with the display monitor 422 supported by a lightweight stand 424. Wheels 427 may be attached to the lightweight stand 424 via a plurality of stabilizing legs 425 for rolling the stand 424 across a surface, such as a floor, together with the processing console 420. A foot pedal assembly 426 having one or more pedals may be configured to initiate and terminate serial radiographic image acquisition (fluoroscopy). The foot pedal assembly 426 may also be configured to switch the mobile radiographic imaging system 400 into alternate radiographic operating modes, such as between a fluoroscopic imaging mode and a standard single image projection radiography mode.

Figure 9:
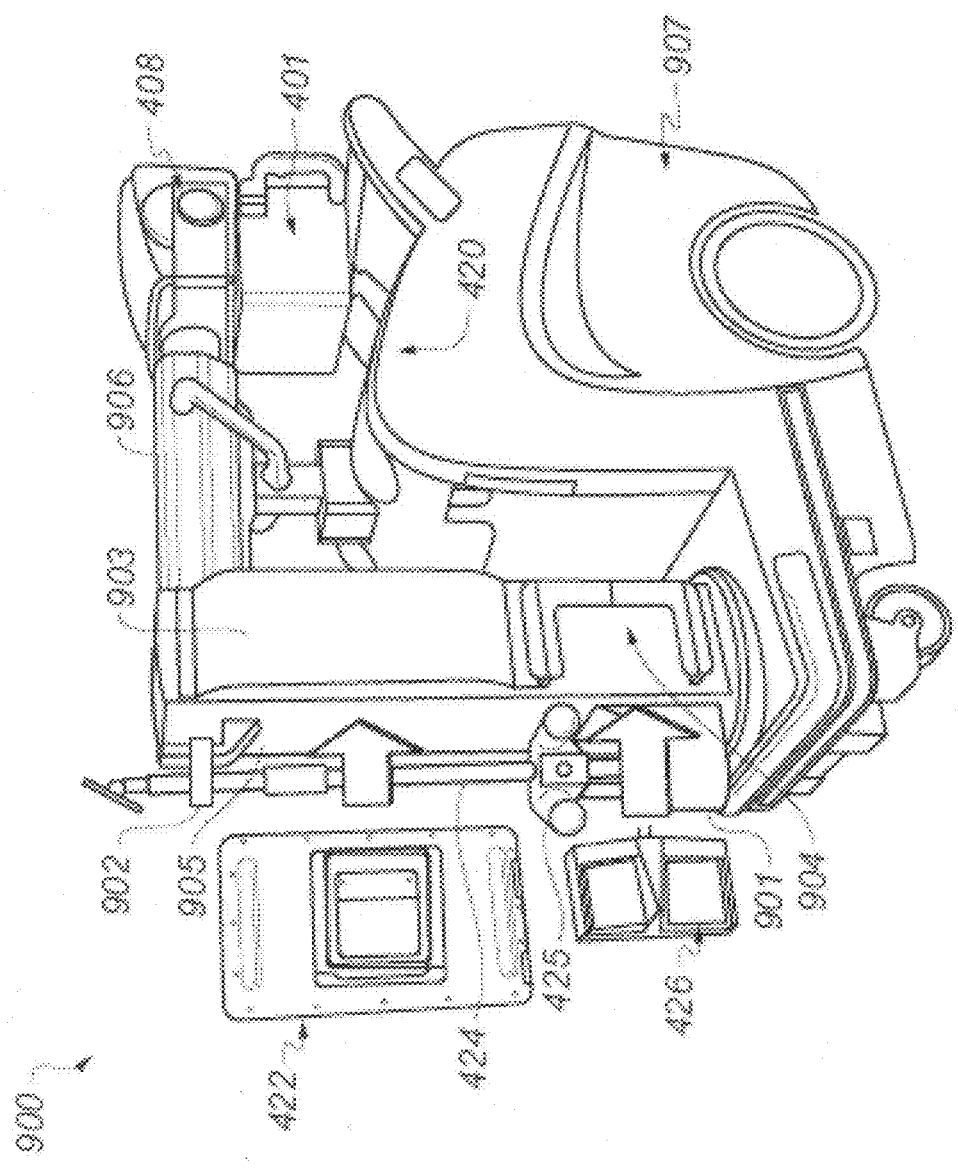
FIG. 9 is a perspective view of a mobile digital radiographic (DR) imaging system.

FIG. 9 is a perspective view of the wheeled mobile x-ray cart 900 of the mobile digital radiographic imaging system 400. FIG. 9 depicts the major components of the mobile radiographic imaging system 400 in their stowed positions on the wheeled mobile x-ray cart 900 which are configured for rollably transporting the mobile radiographic imaging system 400 in a patient care facility. An advantage of the mobile radiographic imaging system 400 is that serial radiography (e.g., fluoroscopy) becomes completely mobile in nature because the necessary components are easily transportable to a patient bedside using the wheeled mobile x-ray cart 900. When it is desired for the mobile radiographic imaging system 400 to be used for general purpose radiography, the hardware described herein for serial radiography may be used for general purpose imaging.

As shown in FIG. 9, a storage nest 901 is configured to store the lightweight stand 424. A feature of the stand 424 is that the stabilization legs 425 can be folded to minimize required space for transport, and storage nest 901 is configured to receive the legs 425 in a folded state. An upper restraint 902 has a nesting feature assembly sized to receive the pole of the stand 424 and includes a flexible strap to secure it. Monitor storage 903 is used to secure the digital display 422 during transport. The digital display 422 may be inserted into the monitor storage 903 in the direction indicated by the corresponding arrow. Monitor storage 903 is formed as a continuous and rounded shape such that it does not snag or inhibit movement of high voltage cables that may drape along the mobile radiographic imaging system 400. Foot pedal assembly storage 904 is used to secure the foot pedal assembly 426 during transport. The foot pedal assembly 426 may be inserted into the foot pedal assembly storage 904 in the direction indicated by the corresponding arrow. A feature of the foot pedal assembly 426 is an external groove configured to receive its connectivity cable before insertion into the foot pedal assembly storage 904. The bottom of the vertical support column 905 is attached to, and is rotatable relative to, the wheeled transport frame 907 which contains the processing console 420. The tube head comprising x-ray source 408 and electronic collimator 401 is attached to one end of a horizontal boom 906 which, in turn, is attached to a top end of the vertical support column 905. The tube head is configured to be movable to a variety of angular positions with respect to horizontal boom 906.

Still referring to FIGS. 6-9, there is described a method of operating a mobile fluoroscopic imaging system wherein an x-ray source and a digital radiography (DR) detector are manually positioned about a patient. Data defining a spatial configuration of the x-ray source and the collimator is stored in the system. The system is configured to determine a source-to-image distance of the x-ray source and the DR detector by activating the x-ray source and capturing a scout image in the DR detector. Dimensions of the scout image are calculated and the source-to-image distance is determined based on the data defining the spatial configuration of the x-ray source and the collimator and on the dimensions of the scout image. In an embodiment, a method of operating a mobile fluoroscopic imaging system includes positioning an x-ray source and a DR detector about a patient. Data defining a spatial configuration of the x-ray source and the collimator is stored in the system. The system is configured to determine a source-to-image distance of the x-ray source and the DR detector including by activating the x-ray source and capturing a scout image in the DR detector.

Dimensions of the scout image are calculated and the source-to-image distance is determined based on the data defining the spatial configuration of the x-ray source and the collimator and on the dimensions of the scout image. In another embodiment, a method of operating a mobile fluoroscopic imaging system having a mounted x-ray source, a collimator, and a freely positionable DR detector includes positioning the x-ray source and the DR detector about a patient.

Inclinometers are provided on the x-ray source and the detector to determine that the x-ray source and the detector are parallel within an acceptable tolerance. An aperture of the collimator is set to a preselected size and a scout image is captured on the DR detector. A size of the radiation field of the scout image on the DR detector is determined and increased aperture size is calculated so that the radiation field of the increased aperture size fits within borders of the DR detector. The aperture is set to the increased size and a fluoroscopic examination is commenced.

Figure 10B:
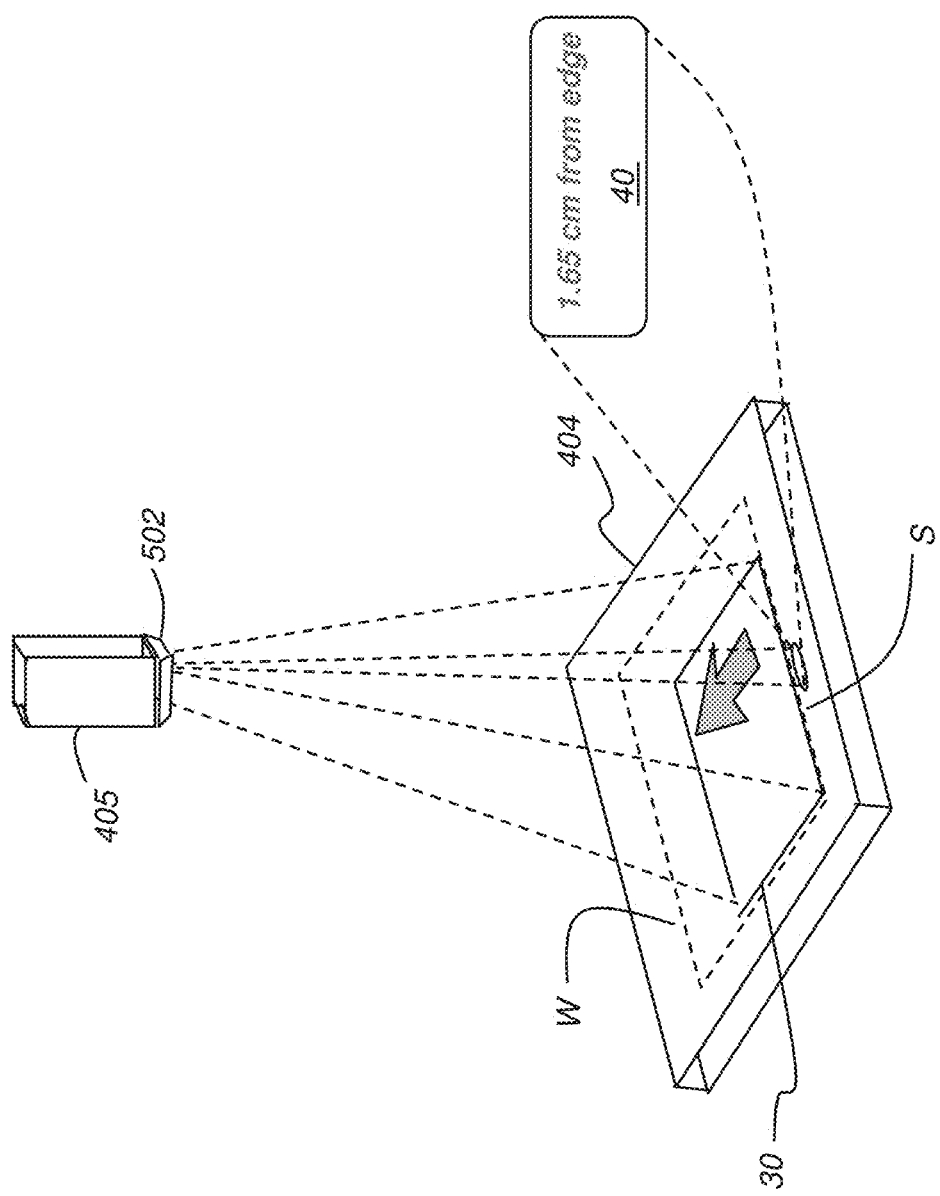
FIG. 10B is a perspective view showing an outline of a radiation field in a Warning zone defined on the detector.
Figure 10C:
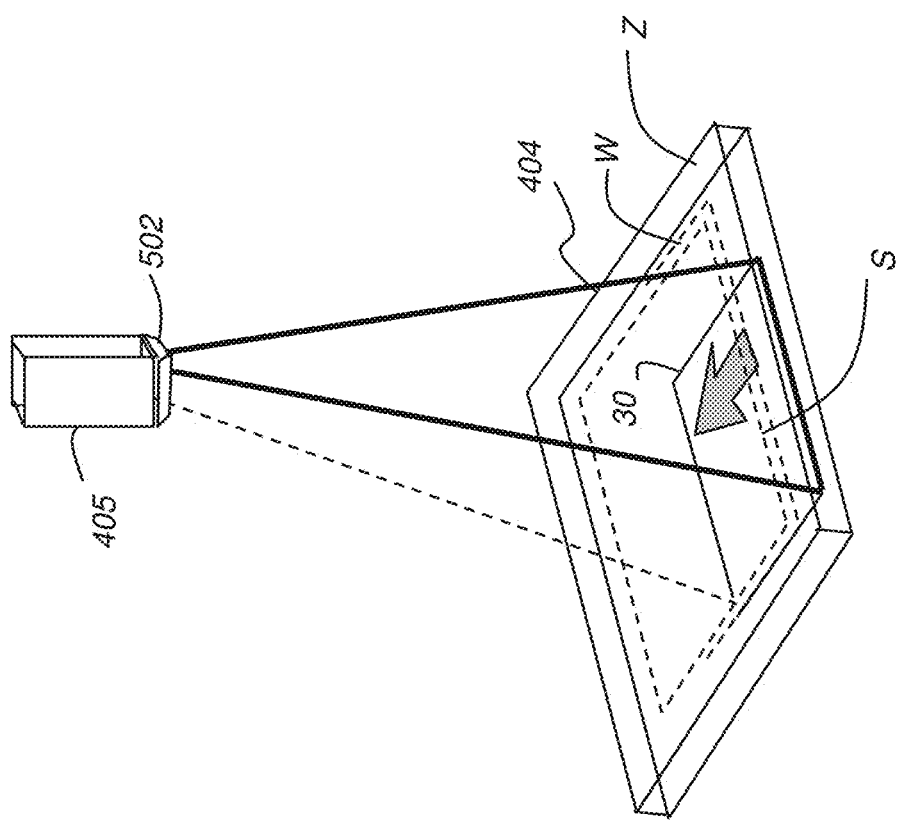
FIG. 10C is a perspective view showing an outline of a radiation field in a Termination zone defined on the detector.

According to an embodiment of the present disclosure, collimator light 502 includes a projector, configured to project information related to radiation beam tracking onto the patient or imaged object during the fluoroscopy session. With this arrangement, the control logic in processing system 421 (FIG. 6) can control the temporal and spatial pattern of illumination from the collimator light 502, according to the detected boundaries of the image content generated at detector 404. FIGS. 10A, 10B, and 10C show some different examples and features for the projected illumination output. For clarity, the patient is not represented in FIGS. 10A-C; in practice, the projected outline 30 and other content can appear displayed on and near the patient. Because edges of the detector 404 may not be clearly perceptible to the operator or practitioner, the projected illumination pattern can be useful for indicating positioning status.

FIG. 10A shows projection of a radiation field outline 30 from collimator light 502 where there is good positioning of the source and detector 404. In the FIG. 10A example, outline 30 indicates that the radiation field bounded by the outline is clearly well within the edges of detector 404 and within the Safe zone S, as described previously. Illumination within and extending to outline 30 can be displayed in an appropriate color to indicate Safe zone positioning, for example.

The example of FIG. 10B shows a change in the projected illumination from collimator light 502 where the scout or fluoroscopy radiation field extends past the boundaries for Safe zone S and into Warning zone W. Collimator illumination can change color accordingly to indicate position status. Further, a portion of outline 30, or the complete outline, can change color to alert the attending staff. A text message 40 can display informative or instructional information that can be used to aid in dynamic adjustment of the tube head position while the fluoroscopy session continues, for example. An arrow or other symbol can be projected as a warning or to indicate a recommended correction.

The example of FIG. 10C shows how projection may change when the radiation field extends past the Warning zone W and into the Termination zone Z, so that emission is suspended. Collimator illumination can change to a suitable color, such as red, to indicate this condition. In addition, where projection apparatus is provided, the color of part or all of outline 30 can be changed to reflect this condition. Similarly, colors and appearance of symbols can also be suitably changed.

Figure 11:
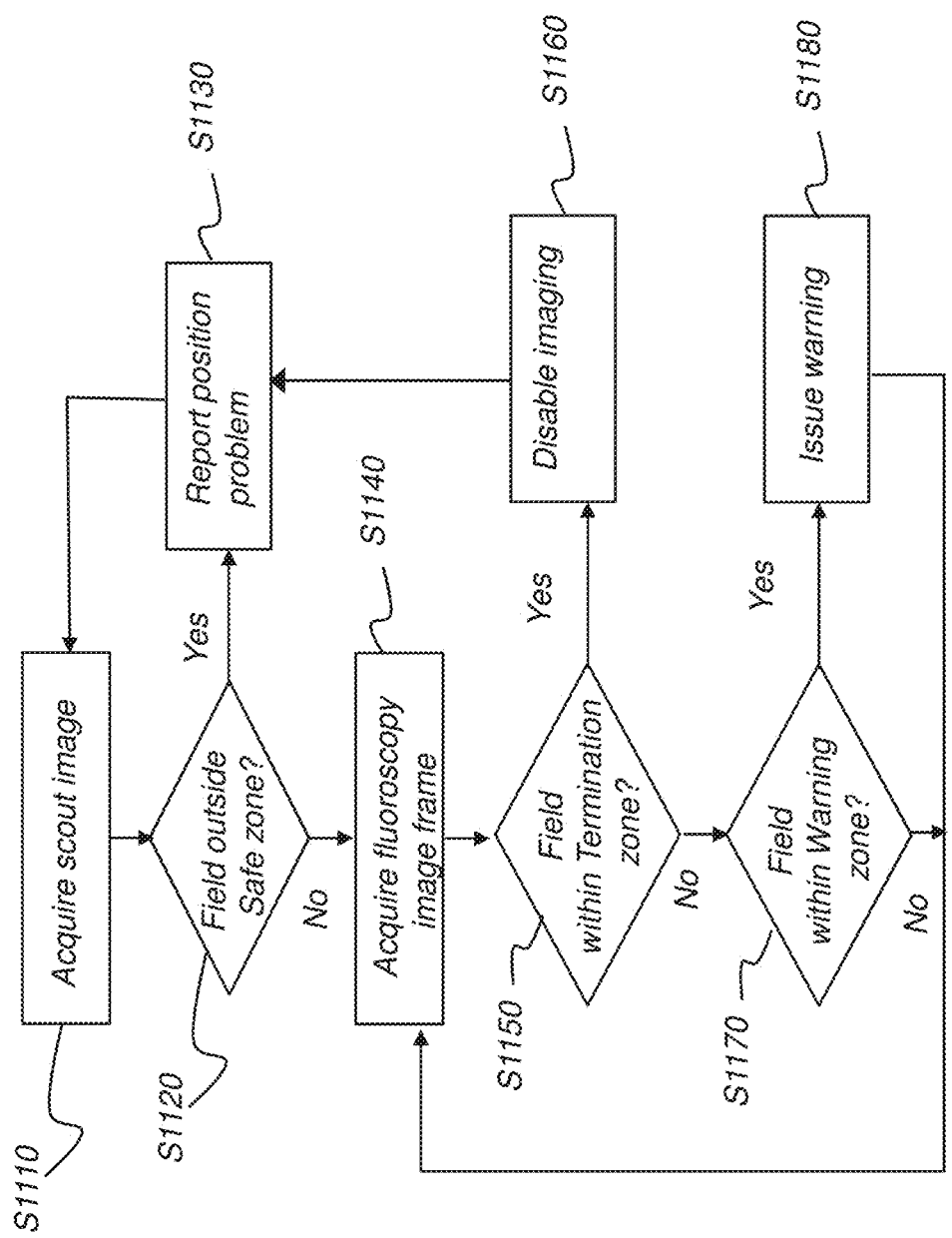
FIG. 11 is a logic flow diagram showing a sequence for fluoroscopy imaging according to an embodiment of the present disclosure.

The logic flow diagram of FIG. 11 shows a sequence for fluoroscopy imaging while tracking the position of the radiation field from the x-ray source. This sequence can be executed by processing system 421 (FIG. 6) before and during the fluoroscopy session. An initial acquisition step S1110 acquires a scout image for checking the position of the radiation field, as recorded by the detector. A field boundary check step S1120 senses and reports the position of the received radiation field, as recorded by the detector, to determine whether or not the field lies fully within the Safe zone S. If outside Safe zone S, a problem reporting step S1130 controls the illuminated content from collimator light 502, such as controlling color, timing, and other appearance factors, as is described with reference to the examples of FIGS. 10A-10C. The operator corrects the positioning error and can acquire a second scout image as shown, repeating steps S1110 and S1120 as needed in order to assure position of the radiation field within the Safe zone S.

Figure 6:
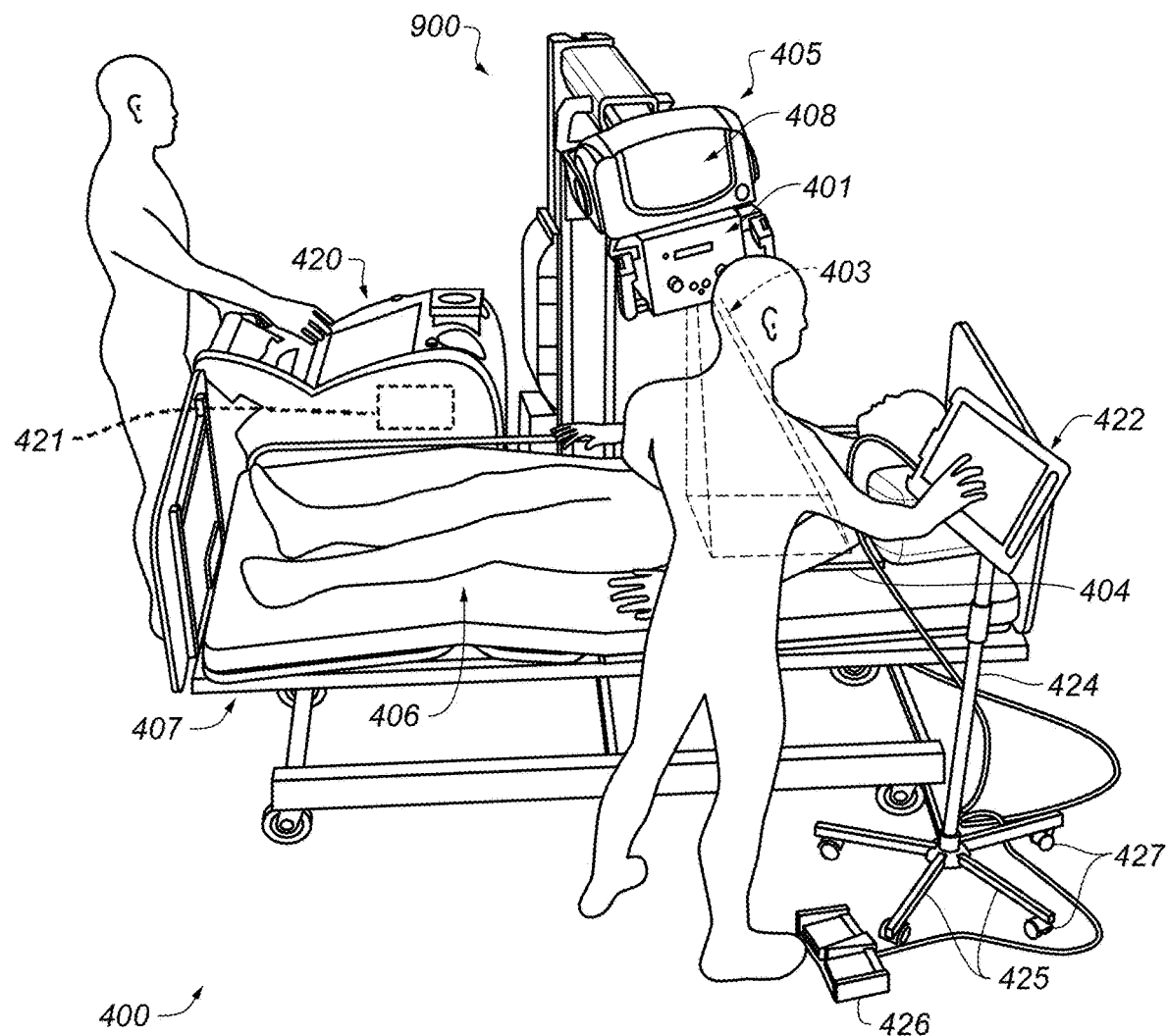
FIG. 6 is a perspective view of a mobile digital radiographic (DR) imaging system.
Figure 7:
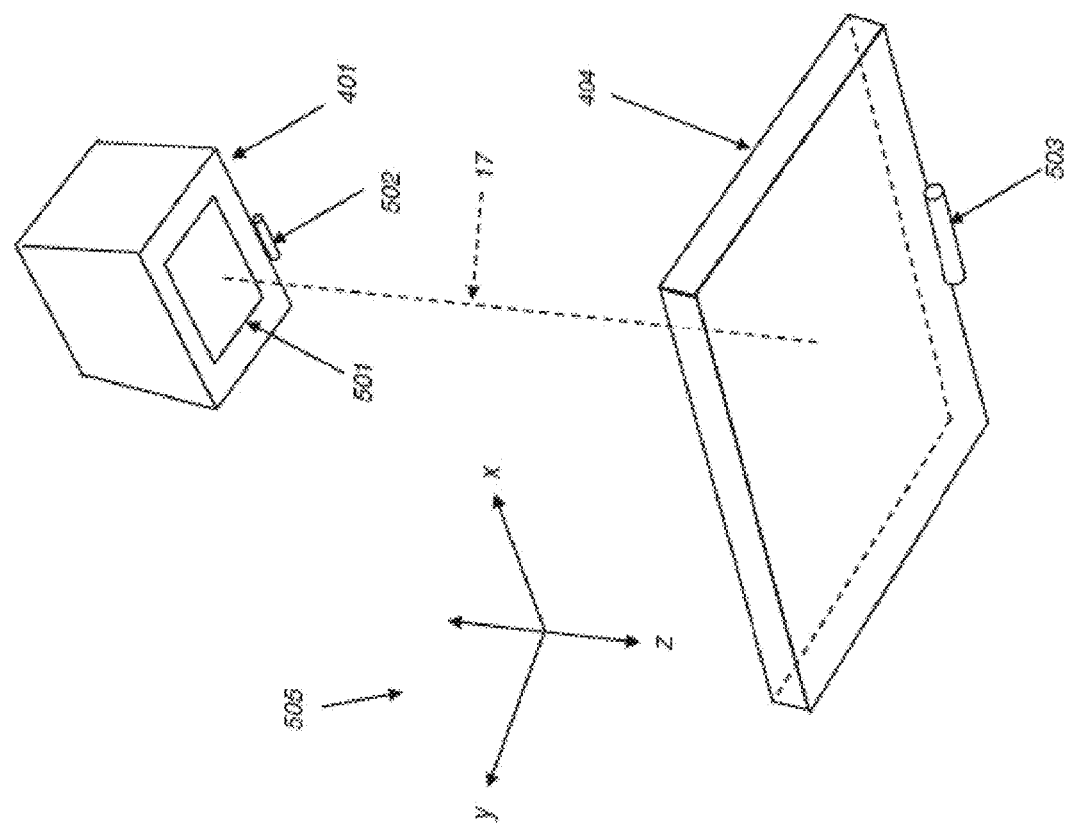
FIG. 7 is a perspective view showing source and detector positioning for a mobile digital radiographic (DR) imaging system.
Figure 8:
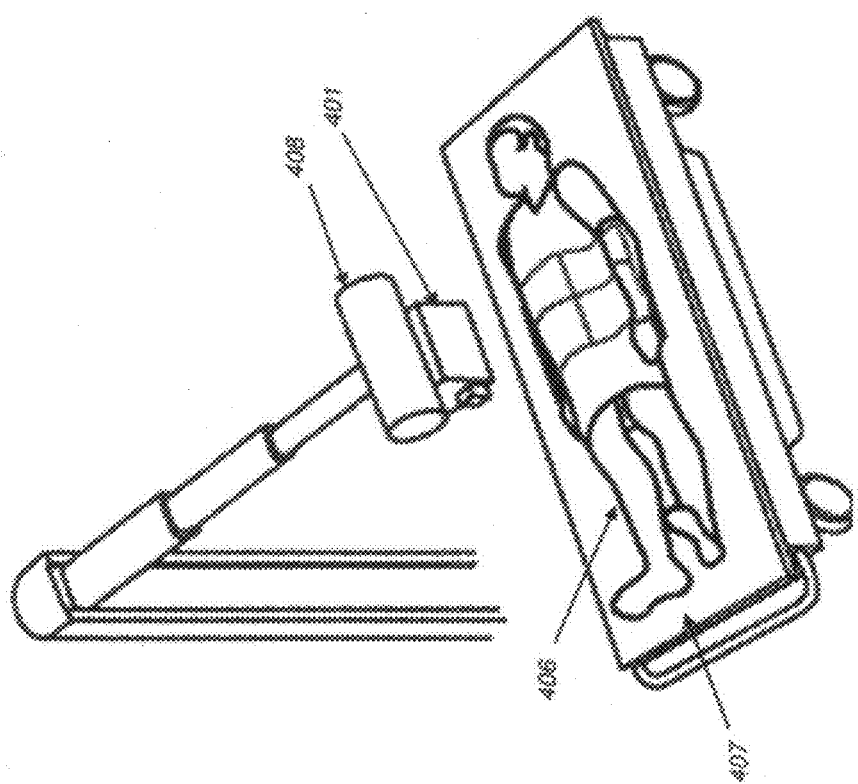
FIG. 8 is a perspective view of patient imaging using a mobile digital radiographic (DR) imaging system.

Once conditions required for initial placement using the scout image have been satisfied, fluoroscopy imaging can commence. Continuing with FIG. 11, a looping sequence follows, continually checking the position of the radiation field throughout fluoroscopy acquisition. An acquisition step S1140 acquires a fluoroscopy image frame. A field boundary check step S1150 determines whether or not the radiation field of the acquired frame is detected within the Termination zone Z; if so, a disable and reporting step S1160 disables radiation emission for fluoroscopy until the field position is set correctly and reports the positioning problem on the control monitor and/or using the collimator light display. For example, step S1160 can disable the operator foot pedal 426 (FIG. 6). If the radiation field does not impinge the Termination zone Z, fluoroscopy can continue. A second field boundary check step S1170 checks for field impingement onto the Warning zone W. A reporting step S1180 displays a warning message or other signal but allows imaging to continue. Processing continues through the loop of steps S1140, S1150, S1160, S1170, and S1180 until the fluoroscopy session is terminated.

It is noted that when fluoroscopy is disabled in step S1160, operation moves to step S1110 for scout image acquisition, enabling the practitioner to make and verify any needed positional adjustments for returning to fluoroscopy.

There can be advantages to allowing the operator to set the boundary thresholds for Safe zone S, Warning zone W, and/or Termination zone Z and to select other operational parameters suitable to the patient and the procedure for which fluoroscopy is used.

Figure 12:
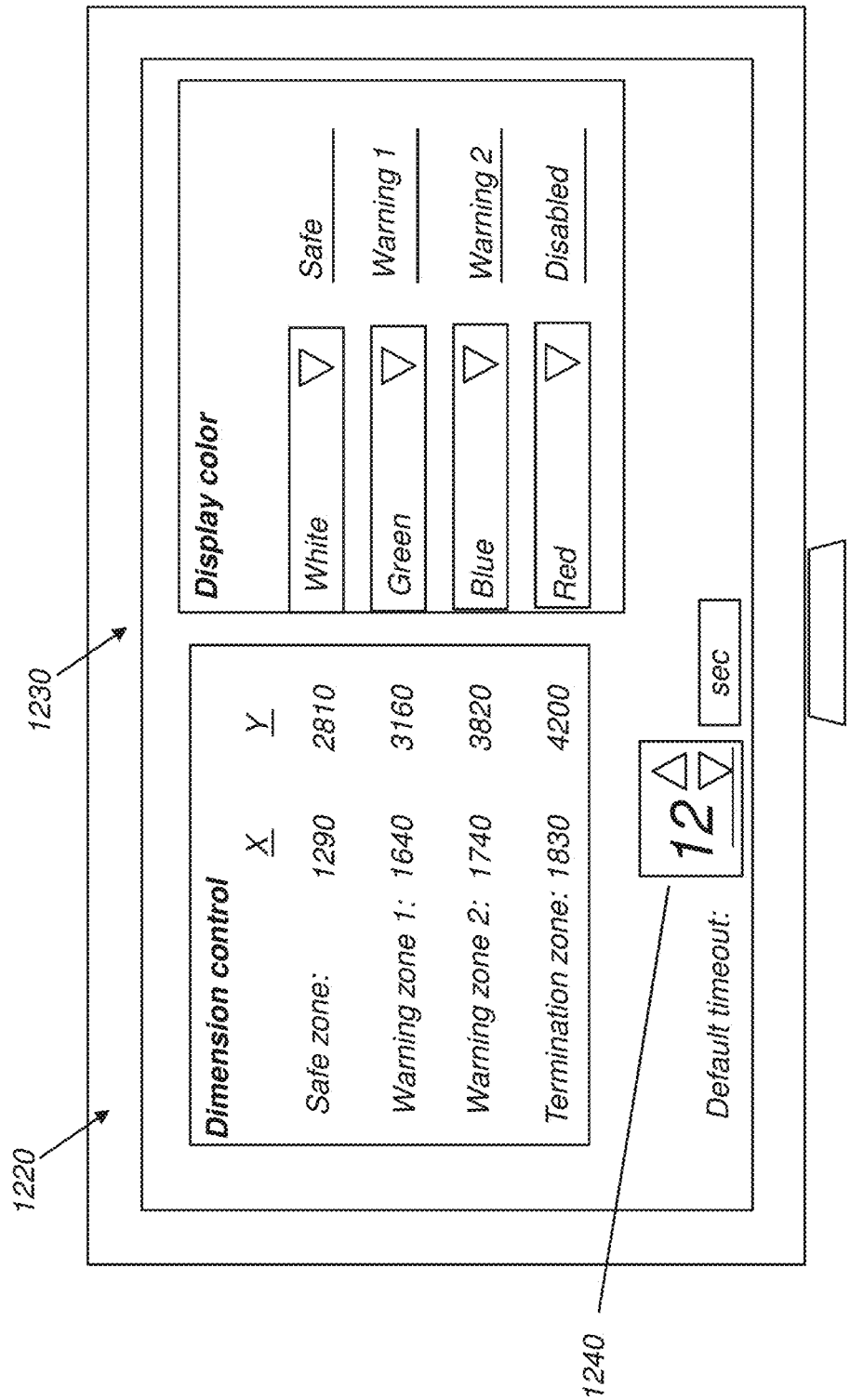
FIG. 12 is a plan view showing an operator interface for zone and parameter setup.

FIG. 12 shows an exemplary operator interface 1210 that allows configuration of dimensions for Safe, Warning, and Termination zones as well as determining the appearance of the projected information from collimator light 502.

A dimension control function 1220 enables adjustment of zones to suit a particular system. As shown in FIG. 12, multiple Warning zones W can be set up, with corresponding thresholds and behavior settings. Values can be set up according to various dimensional metrics, such as inches, millimeters, number of pixels, percentage of active detector area, or other criteria.

A display control function 1230 controls the appearance of the projected collimation light for radiation field representation or outline, message content, and other features.

According to an embodiment of the present disclosure, a timeout entry 1240 can be provided in order to momentarily delay termination of radiation emission when the radiation field has been detected within the Termination zone Z. The default timeout can be preset at manufacture or can be operator-configurable. An optional second timeout can be set by the operator, to allow an operator override, such as at some time during the fluoroscopy session. This second timeout can add a measure of time in addition to the default timeout. Time periods can alternately be measured in terms of total dose or number of image frames. Alternately, time periods used can be clock time for x-ray enablement, independent of actual exposure time. The timeout period can vary based on factors such as relative area of the radiation field that is detected outside Safe zone S, for example.

According to an embodiment of the present disclosure, a weighted timeout is provided based on percentage area of the radiation field within the Safe zone S or Warning zone W. Thus, for example, the full timeout period applies when less than 2-4% of the radiation field is detected within Warning zone W and the balance of the field lies within Safe zone S.

The timeout period is reduced, such as in proportion, as the amount of the radiation field detected outside Safe zone S decreases, or inversely as the amount within Warning zone W increases.

In this disclosure, an embodiment of the present disclosure may be described as a software program. Those skilled in the art will recognize that the equivalent of such software may also be constructed in hardware. Because image manipulation algorithms and systems are well known, the present description will be directed in particular to algorithms and systems forming part of, or cooperating more directly with, the method in accordance with the present disclosure. Other aspects of such algorithms and systems, and hardware and/or software for producing and otherwise processing the image signals involved therewith, not specifically shown or described herein may be selected from such systems, algorithms, components and elements known in the art.

A computer program product may include one or more non-transitory storage medium, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present disclosure.

The methods described above may be described with reference to a flowchart. Describing the methods by reference to a flowchart enables one skilled in the art to develop such programs, firmware, or hardware, including such instructions to carry out the methods on suitable computers, executing the instructions from computer-readable media. Similarly, the methods performed by the service computer programs, firmware, or hardware are also composed of computer-executable instructions.

The invention claimed is:

1. A method for fluoroscopy, comprising:
   energizing a radiation source to form a scout image on a detector;
   processing the scout image to determine and report a radiation field position with respect to a predetermined zone of the detector;
   energizing the radiation source for fluoroscopy imaging of a subject when the reported radiation field position is fully within the predetermined zone; and
   determining the position of the radiation field with respect to a warning zone defined for the detector and providing a warning when the radiation field is detected within the warning zone.

2. The method of claim 1 further comprising determining the position of the radiation field with respect to a termination zone defined for the detector and preventing energizing of the radiation source for fluoroscopy when the radiation field is detected within the termination zone.

3. The method of claim 2 further comprising energizing the radiation source in response to entry of an operator override instruction.

4. The method of claim 1 further comprising illuminating the radiation field position with respect to the subject.

5. The method of claim 4 wherein said illuminating the radiation field position further comprises changing the appearance of the illumination according to the reported radiation field position.

6. The method of claim 5 wherein said changing the appearance comprises changing a color of the illumination.

7. The method of claim 4 wherein said illuminating the radiation field position further comprises changing the appearance of the illumination according to scout image or fluoroscopy acquisition.

8. The method of claim 7 wherein said changing the appearance comprises changing a color of the illumination.

9. The method of claim 1 further comprising acquiring the scout image and fluoroscopy imaging at the same radiation field position.

10. The method of claim 1 wherein the scout image is formed using a first set of technique settings and fluoroscopy imaging uses a second set of technique settings.

11. The method of claim 1 further comprising displaying an outline of the radiation field position as reported by said processing.

12. The method of claim 1 further comprising automatically adjusting dimensions of the radiation field according to the reported radiation field position.

13. A method for fluoroscopy, comprising:
energizing a radiation source to form a scout image on a detector;
processing the scout image to determine and report a radiation field position with respect to a predetermined zone of the detector;
energizing the radiation source for fluoroscopy imaging of a subject when the reported radiation field position is fully within the predetermined zone; and
determining the position of the radiation field with respect to a termination zone defined for the detector and suspending energization of the radiation source after detection of the radiation field within the termination zone.

14. A method for fluoroscopy, comprising:
energizing a radiation source to form a scout image on a detector;
processing the scout image to determine and report a radiation field position with respect to a predetermined zone of the detector;
energizing the radiation source for fluoroscopy imaging of a subject when the reported radiation field position is fully within the predetermined zone;
displaying the fluoroscopy image that is generated according to the radiation field position; and
processing the generated fluoroscopy image and providing a warning related to detection of the radiation field position within a predefined warning zone on the detector.

15. A method for fluoroscopy, comprising:
energizing a radiation source to form a scout image on a detector;
processing the scout image to determine and report a radiation field position with respect to a predetermined zone of the detector;
energizing the radiation source for fluoroscopy imaging of a subject when the reported radiation field position is fully within the predetermined zone;
displaying the fluoroscopy image that is generated according to the radiation field position; and
processing the generated fluoroscopy image and suspending energization of the radiation source for fluoroscopy after detection of the radiation field position within a predefined termination zone on the detector.

16. The method of claim 15 wherein said suspending energization of the radiation source is delayed according to a predetermined timeout.

17. The method of claim 15 further comprising delaying suspension of energization of the radiation source in response to a first operator override.

18. The method of claim 17 wherein the first operator override has a predetermined time limit.

19. The method of claim 17 further comprising re-energizing the radiation source in response to a second operator override.

20. A method for fluoroscopy, comprising iteratively:
acquiring, on a digital radiation detector, a fluoroscopy image that is generated according to an emitted radiation field;
providing a warning signal when the emitted radiation field impinges a predefined warning zone on the detector.

21. The method of claim 20 further comprising:
terminating acquisition of the image if the emitted radiation field impinges on a predefined termination zone on the detector.

22. The method of claim 21 further comprising accepting an operator-entered dimension defining either the warning or termination zone.

23. The method of claim 21 wherein said terminating occurs following a timeout period, and wherein the timeout period is predetermined by an operator.

24. The method of claim 20 wherein the warning signal is projected onto a subject.

* * * * *